United States Patent [19]

Creuzet et al.

[11] Patent Number: 4,591,600

[45] Date of Patent: May 27, 1986

[54] 3-HYDROXYFLAVONES: THEIR PREPARATION AND THERAPEUTIC APPLICATION

[75] Inventors: Marie-Helene Creuzet, Bordeaux; Claude Feniou, Pessac; Françoise Guichard, Bordeaux; Gisele Prat, Talence; Jacqueline Mosser, Saint-Medard-En-Jalles; Henri Pontagnier, Pessac, all of France

[73] Assignee: Societe Cortial, S.A., Paris, France

[21] Appl. No.: 594,976

[22] Filed: Mar. 29, 1984

[30] Foreign Application Priority Data

Apr. 1, 1983 [FR] France .................... 83 05567

[51] Int. Cl.$^4$ ..................... A61K 31/35; C07D 311/32
[52] U.S. Cl. ..................... 514/456; 549/403
[58] Field of Search ................ 549/403; 514/456

[56] References Cited

U.S. PATENT DOCUMENTS

| | | | |
|---|---|---|---|
| 2,892,845 | 6/1959 | Jurd | 549/403 |
| 2,892,846 | 6/1959 | Jurd | 549/403 |
| 3,450,717 | 6/1969 | Krämer et al. | 549/403 |
| 4,532,254 | 7/1985 | Okuda et al. | 514/456 |

FOREIGN PATENT DOCUMENTS 520376  1/1956  Canada ................... 549/403

*Primary Examiner*—Ethel G. Love
*Attorney, Agent, or Firm*—Oblon, Fisher, Spivak, McClelland & Maier

[57] ABSTRACT

This invention relates to quercetin or fisetin derivatives substituted on the oxygen in the 3 position by groups such as lower alkyl, cycloalkyl, methanesulfonyl or paratoluenesulfonyl.

The derivatives substituted by methanesulfonyl or paratoluenesulfonyl are obtained from a 3-O-glycoside whose phenol OH groups are blocked in the form of benzoate, and from which the OH in the 3 position is released by the action of concentrated HCl; this OH is esterified by mesityl chloride or paratoluenesulfonic acid chloride, and the benzoate groups are eliminated by soda treatment. The O derivatives substituted by alkyl or cycloakyl are prepared from a suitably substituted acetonitrile or metadiphenol; the resulting derivative reacts with 3,4-dibenzyloxybenzoic acid and the resulting flavone is debenzylated by hydrogenolysis.

The derivatives, object of this invention, are useful in preventive or curative therapy of ocular and nervous complications from diabetes and are also useful as hypolipidemic or hypoglycemic agents.

10 Claims, No Drawings

3-HYDROXYFLAVONES: THEIR PREPARATION AND THERAPEUTIC APPLICATION

BACKGROUND OF THE INVENTION

1. Field of the Invention

This invention relates to new 3-hydroxyflavones variously substituted on the oxygen in the 3 position, the method of preparing them and their therapeutic application.

The new products, which are the object of this invention, have the general formula

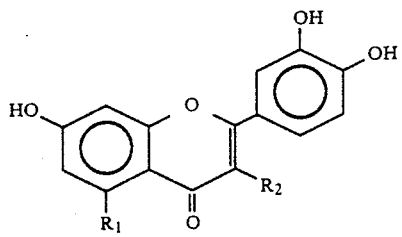

where $R_1$ is H or OH and $R_2$ is a lower alkoxy of $C_2$ to $C_6$, a cycloalkoxy of $C_5$ to $C_8$, a methanesulfonyloxy or a paratoluenesulfonyloxy, provided that $R_1$ is not OH if $R_2$ is a lower alkoxy of $C_2$ to $C_4$.

The products where $R_1$ is OH are quercetin derivatives; the products where $R_1$ is H are fisetin derivatives.

Some methyl ethers of flavonols and in particular 3-O-methyl flavanols are already known. A certain number of these are natural derivatives. The Biosedra company on May 21, 1970 under No. 70 18458 patented pentabenzylquercetin used in therapy in the standard indications of flavonoids (inhibition of hyperpermeability and reduction of capillary fragility).

The Hoffman-la-Roche company filed on 4/9/1980, under British priority of 4/10/1979, a European Pat. No. 19081 describing 3-alkoxy-5,7-dihydroxyflavones having antiviral activity and in particular products answering general formula I with $R_1$ being OH and $R_2$ being a lower alkoxy of $C_1$ to $C_4$ and preferably equal to methoxy or ethoxy. These products are, however, distinct from the compounds of the present invention.

SUMMARY OF THE INVENTION

We have now discovered that the flavones of formula I with $R_1$ being H or OH and $R_2$ being a lower alkoxy of $C_2$ to $C_6$, a cycloalkoxy of $C_5$ to $C_8$, a methanesulfonyloxy or paratoluenesulfonyloxy, provided that $R_1$ is different from OH if $R_2$ is a lower alkoxy of $C_2$ to $C_4$, exhibit properties inhibitive of aldose reductase, making possible their use in the prevention of complications, ocular and nervous particularly, from diabetes. These new products are also useful as hypoglycemic and hypolipidemic agents.

DESCRIPTION OF THE PREFERRED EMBODIMENTS

These products which are the object of this invention, are prepared as follows:

The products of formula I where $R_2$ is methanesulfonyloxy or paratoluenesulfonyloxy are prepared for example from flavone glycosides with $R_1$ being H or OH and $R_2$ being O-glycosyl. The free phenol groups of the glycoside are blocked, for example, in the form of benzoic esters and the aglycone is obtained by the action of concentrated hydrochloric acid. The flavonol 3-OH group is then esterified by mesityl chloride or paratoluenesulfonic acid chloride. The benzoate groups are eliminated by soda treatment.

The products of formula I where $R_1$ is H or OH and $R_2$ is a lower alkoxy of $C_2$ to $C_6$ or cycloalkoxy of $C_5$ to $C_8$, provided that $R_1$ is not OH if $R_2$ is a lower alkoxy of $C_2$ to $C_4$, are prepared by action of a derivative of formula

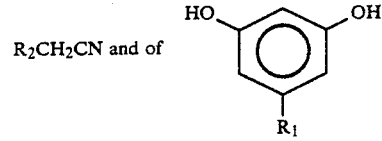

in the presence of hydrochloric acid leading to

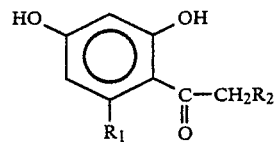

This derivative reacts with 3,4-dibenzyloxybenzoic acid anhydride to lead to a product of formula

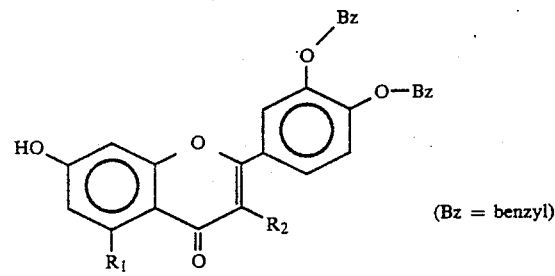

(Bz = benzyl)

This ether is transformed into a formula I product by hydrogenolysis in the presence of a hydrogenation catalyst: for example, of palladium/$BaSO_4$.

This invention will now be illustrated by the following examples which are not meant to be limiting of the invention.

EXAMPLE 1

Synthesis of 3-cyclohexyloxy-5,7-3',4'-tetrahydroxyflavone; product of formula I with $R_1$ is OH, $R_2$ is

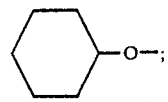

code name COR 1983.

1a. Synthesis of cyclohexyloxyacetonitrile 100 g of cyclohexanol, 40 g of trioxane, 200 cc of toluene are introduced in a 500-cc Grignard reactor. This mixture is brought to 0° C. with stirring. Gaseous hydrochloric acid is bubbled for four hours. The water that is formed is decanted.

The chloromethoxycyclohexane is dried then distilled. BP=75° C. under 27 millibars. A mixture made up of 62 g of this derivative and 56 g of cuprous cyanide is refluxed at 120° C. for four hours. The cyclohexyloxyacetonitrile is distilled. BP=60°-70° C. under 0.014 millibar. Yield 75%.

1b. Synthesis of 2-cyclohexylglycoloyl phloroglucinol 20 g of cyclohexyloxyacetonitrile and 18 g of anhydrous phloroglucinol are dissolved in 500 cc of anhydrous ether. Gaseous hydrochloric acid is bubbled for 4 hours at 0° C. and it is kept overnight at 0° C. with stirring. It is filtered. The ketimine hydrochloride is taken up in 250 cc of boiling ethyl alcohol, and 250 cc of hot water are added. The mixture is refluxed for three hours. The reaction is followed by thin-layer chromatography. After cooling, the 2-cyclohexylglycoyl phloroglucinol separates as an oil, then crystallizes. It is recrystallized in an alcohol/water mixture, taken up in chloroform, then precipitated in petroleum ether. Yield 60%.

1c. Synthesis of 3,4-dibenzyloxybenzoic acid anhydride 138 g of 3,4-dihydroxybenzaldehyde, 138 g of potassium carbonate and one liter of dimethylformamide (DMF) are introduced in a 2-liter Grignard reactor. The mixture is refluxed with stirring. 253 g chloromethylbenzene are added drop by drop. The mixture is refluxed with stirring for 6 hours. After cooling, the salt that has precipitated is filtered and washed in a little DMF. The reaction medium is then poured by small amounts into 15 liters of ice water with good stirring. 3,4-Dibenzyloxybenzaldehyde precipitates as a paste, then crystallizes. The solid is filtered, then taken up in boiling methyl alcohol. After a hot filtering; the methyl alcohol solution is cooled with stirring, and the precipitate that is formed is filtered, washed with iced methyl alcohol, ethyl ether, then dried. Yield 77%.

A 1.5 liter solution of water, containing 700 cc of pyridine, and 245 g of 3,4-dibenzyloxybenzaldehyde is refluxed in a 4-liter round-bottom flask. 162 g of potassium permaganate are added little by little. The mixture is refluxed for an hour then filtered hot and washed with a liter of boiling water. The first filtrate is concentrated to eliminate the pyridine. After acidification with $H_2SO_4$ at ½ of all the filtrates, the precipitate is filtered then washed with water and dried. Yield 85%.

A one liter solution of benzene, containing 130 g of 3,4-dibenzyloxybenzoic acid and 45 cc of thionyl chloride is refluxed for two hours with stirring. After evaporation and taking up in ether, the acid chloride is filtered and washed with cold ether. Yield 90%.

The mixture consisting of 1.5 liter of anhydrous ether, 290 cc of pyridine, 100.2 g of 3,4-dibenzyloxybenzoic acid and 105.7 g of 3,4-dibenzyloxybenzoic acid chloride is stirred for 24 hours at ambient temperature in a round-bottom flask provided with a drying tube. The mixture is then poured in 8 liters of ice water. After 45 min stirring the precipitate is filtered, washed with one liter of 0.1N iced hydrochloric acid, one liter of iced 0.1N $Na_2CO_3$, then one liter of ice water. The solid is solubilized in $CHCl_3$; it is decanted, dried and evaporated and the anhydride is recrystallized in ethyl acetate. Yield 88%.

1d. Synthesis of 3',4'-dibenzylozy-5,7-dihydroxy-3-cyclohexyloxyflavone 13.3 g of 2-cyclohexylglycoyl phlorogucinol prepared according to 1b, 130 g of anhydride prepared according to 1c and 28 cc of trimethylamine are introduced in a 2-liter round-bottom flask. The reaction mixture is immersed in a bath at 170° C. It is heated for 3 hours with stirring then cooled to 100° C. After addition of 1 liter of methyl alcohol then 60 cc of 60% potash, it is refluxed 45 min. After cooling at 30° C., 1.5 liters of cold water are added. The precipitate that is formed is filtered. The aqueous phase is extracted 3 times with ether. The solution is brought to pH 10 with a $CO_2$ current, extracted three times with ethyl acetate. The organic phase is dried, evaporated. The residue is taken up in ether. Yield 64%.

1e. Synthesis of 3-cyclohexyloxy-5,7,3',4'-tetrahydroxyflavone 27 g of 3',4'-dibenzyloxy-5,7-dihydroxy-3-cyclohexyloxyflavone, 500 cc of acetone, 500 cc of methyl alcohol, 8 spatulas of palladium on 5% $BaSO_4$ are introduced in a 2-liter round-bottom flask. The mixture is stirred under an hydrogen atmosphere for 3 hours. The reaction is followed with thin-layer chromatography. After filtering on millipores, the solution is evaporated. Yield 98%.

NMR spectrum in DMSO(D6): $\delta=0.8-2.3$ ppm, 10 protons, complex multiplet, $CH_2$; $\delta=4.0-4.6$ ppm, 1 proton, complex multiplet, H—C—O—; $\delta=6.2$ ppm, 1 proton, doublet, H-6; $\delta=6.4$ ppm, 1 proton, doublet, H-8; $\delta=6.9$ ppm, 1 proton, doublet, H-5'; $\delta=7.3-7.8$ ppm, 2 protons, complex multiplet, H-2'+H-6'; $\delta=9.9$ ppm, 3 protons, dome, OH-7+OH-3'+OH-4', (interchangeable with $D_2O$); $\delta=12.8$ ppm, 1 proton, singlet, OH-5 (interchangeable with $D_2O$).

MP=260°-270° C. (Kofler bench).

Elementary microanalysis: calculated: C 65.62%; H 5.24%; O 29.13%; found: C 65.63%; H 5.30%; O 29.40%.

3-Ethoxy-7,3',4'trihydroxyflavone, formula I product with $R_1=H$ and $R_2=OC_2H_5$, is prepared in the same way; code name COR 1987.

NMR spectrum in DMSO(D6): $\delta=1.3$ ppm, 3 protons, triplet, $CH_3$; $\delta=4.1$ ppm, 2 protons, quadruplet, $CH_2$; $\delta=6.7-8.1$ ppm, 6 protons, complex multiplet, aromatic protons; $\delta=9.9$ ppm, 3 protons, broad peak, OH, (interchangeable with $D_2O$).

MP=254° C. (Mettler apparatus).

EXAMPLE 2

Synthesis of 3-methanesulfonyloxy-3',4',5,7-tetrahydroxyflavone; formula I product with $R_1=OH$, $R_2=CH_3—SO_2—O$; code name COR 1988.

2a. Synthesis of 3',4',5,7-tetrabenzoyloxyflavone 800 g of potassium carbonate are dissolved in 7 liters of water. 100 g of rutin are added with stirring. When the mixture has become limpid, 400 cc of benzoyl chloride are added twice. The mixture is kept under vigorous stirring for two hours. The solid is filtered and washed until neutral. It is dried in vacuo over $P_2O_5$, then put in suspension in 3 to 4 liters of ethyl alcohol; the mixture is stirred vigorously. The solid is filtered and this operation is performed a second time. 205 g of resulting crude rutin tetrabenzoate are dissolved in 1.3 liters of boiling ethyl alcohol. 400 cc of concentrated hydrochloride acid are added once. The mixture is stirred while refluxing the ethyl alcohol for one hour. The alcohol phase is separated from the solid which has precipitated as a viscous mass. The solid is ground in a mortar and washed with water then dissolved in chloroform. After washing with water, drying and evaporation, the residue is taken up in 700 cc of acetone. The mixture of brought to reflux with stirring, filtered hot. The solid is washed with a little acetone. Yield 28.2% (in relation to the rutin).

2b. Synthesis of 3-methanesulfonyloxy-3',4',5,7-tetrahydroxyflavone 49 g of quercetin tetrabenzoate are dissolved in 180 cc of pyridine. 10 cc of mesityl chloride are added. The mixture is kept at ambient temperature for an hour with stirring. A new amount of 10 cc of mesityl chloride is added and stirring is continued at ambient temperature for three hours. The mixture is poured in ice water with stirring. After filtering, the solid is washed with water, dissolved in chloroform. The chloroform phase is dried and evaporated. 600 cc of acetone are added to the evaporation residue. The mixture is brought to reflux with stirring then filtered hot. Yield 54.3%.

8 g of 3-methanesulfonyloxyflavone tetrabenzoate are dissolved in a mixture of 1.5 liters of acetone and boiling methyl alcohol under argon. 2 g of soda dissolved in methyl alcohol are added to the reaction mixture. After determination by thin-layer chromatography that the reaction is complete, the mixture is cooled and the pH is brought to 9 with a $CO_2$ current. The solvents are evaporated. Ethyl acetate is added to the residue. The mixture is subjected to stirring, then the solvent is decanted. The residue is solubilized in water. The solution is neutralized by using $CO_2$ and the precipitate is filtered. It is dried in vacuo over $P_2O_5$. Yield 38%.

NMR spectrum in DMSO(D6): $\delta = 3.5$ ppm, 3 protons, singlet, $CH_3$; $\delta = 6.3$ ppm, 1 proton, doublet, H-6; $\delta = 6.5$ ppm, 1 proton, 1 doublet, H-8; $\delta = 7.0$ ppm, 1 proton, 1 doublet, H-5'; $\delta = 7.3$-7.7 ppm, 2 protons, complex multiplet, H-2'+H-6'; $\delta = 10.0$ ppm, 3 protons, dome, OH-7+OH-3'+OH-4', (interchangeable with $D_2O$); $\delta = 12.1$ ppm, 1 proton, dome, OH-5, (interchangeable with $D_2O$).

MP = 233° C. (Mettler apparatus).

3-Paratoluenesulfonyloxy-5,7,3',4'-tetrahydroxyflavone, a formula I product with $R_1 = OH$ and $R_2 = $ paratoluenesulfonyloxy, is prepared in the same way; code name COR 1990.

The pharmacological properties of the products, object of the invention, are disclosed below.

The advantage of the products of this invention in treatment and prophylaxis of complications from diabetes were shown in vitro by determination of the inhibitive activity of aldose reductase and in vivo in the model of neuropathy induced by streptozotocin.

Inhibition of aldose reductase in vitro

The enzyme was extracted from beef crystalline lenses by the method described by S. Hayman and J. H. Kinoshita (*J. Biol. Chem.* 1965, 240, (2), 877). The percentage of inhibition of the capacity of the enzyme to reduce glyceraldehyde to glycerol under the effect of the product to be tested was determined by spectrophotometric determination of the amount of NADPH reacting according to the method described by Hayman and Kinoshita. We give below in parenthesis after each product the value of the log 1 CI50 where CI50 represents the concentration expressed in mole/1 causing 50% inhibition of the enzymatic activity: COR 1983 (5.8), COR 1987 (6.3), COR 1988 (6.6), COR 1990 (5.5). These values are to be compared with the corresponding value for quercetin (5.0).

Streptozotocin neuropathy 4 batches of 10 rats weighing about 200 g were treated from D−2 to D+3 with a gummy julep of the product to be tested. At D 0 the animals received an i.p. injection of 100 mg/kg of streptozotocin dissolved in a citrate buffer. The glycemia was determined 24 hours and 3 days after injection of the diabetogenic agent. The rats were sacrificed on the 3rd day after streptozotocin injection and the sciatic nerves were removed to determine the sorbitol and inositol levels. Tested under these condition, COR 1988 caused a reduction of the sorbitol level that went from $0.819 \pm 0.215$ mg/kg in the controls to $0.608 \pm 0.049$ mg/kg in animals treated with 50 mg/kg and to $0.482 \pm 0.091$ mg/kg in animals treated with 100 mg/kg. Also the inositol level went from $2.174 \pm 0.481$ mg/kg in the controls to $1.593 \pm 0.109$ mg/kg in the animals treated wtih 25 mg/kg, to $1.430 + 0.104$ mg/kg in the animals treated with 50 mg/kg and to $1.402 \pm 0.130$ mg/kg in animals treated with 100 mg/kg. The sorbitol and inositol levels after treatment were compared with the control levels by the U test of Mann and Whitney (D. Schwartz, Methodes statistique a l' usage des medecins et biologists [Statistical method for use by physicians and biologistes], Ed. Flammarion, Paris 1963). The results obtained are significant with $p < 1\%$. Glycemia of the control animals was $4.72 \pm 0.60$ g/l on D 3. It went to $3.93 \pm 0.82$ g/l in animals treated with 50 mg/g of COR 1988 and to $3.61 \pm 0.73$ g/l in animals treated with 100 mg/kg. The reduction of glycemia are significant.

The toxicity of the products of this invention was determined in mice.

COR 1983 administered orally in solution in water in the presence of 6% gum caused no mortality in a dose of 1 g/kg. Administered intraperitoneally in solution in 5% Tween it did not cause any mortality up to 100 mg/kg and caused 10% mortality in a dose of 200 mg/kg.

COR 1988 administered orally in solution in water in the presence of 6% gum did not cause any mortality up to a dose of 3 g/kg.

The products, object of this invention, are useful as hypolipidemic agents. Thus, COR 1983 administered twice in a dose of 400 mg/kg orally at 20 hour intervals in hypercholesterolemic mice caused 24% reduction in cholesterolemia.

Considering their properties, combined with a slight toxicity, the products according to the invention are useful in human and veterinary therapy, for example, in treatment and prevention of ocular and nervous complications from diabetes and in treatment of diabetes and hyperlipidemias. The products, object of this invention, can be used alone or in association with antidiabetic agents. They will be administered, associated with suitable vehicles and excipients, orally as sugar-coated pills, tablets, syrup, drinkable ampoules; rectally as suppositories; parenterally in subcutaneous, intramuscular, intravenous injections; topically as ointments or gels. They can also be incorporated in compositions for ophthalmic use as collyria and ointments. The doses administered will vary depending on the indication and patient from 5 to 500 mg/d in 2 to 6 doses taken orally, from 5 to 500 mg/d in one or two doses rectally, from 0.5 to 50 mg per injection parenterally.

What is claimed as new and desired to be secured by Letters Patent of the United States is:

1. A compound of the formula

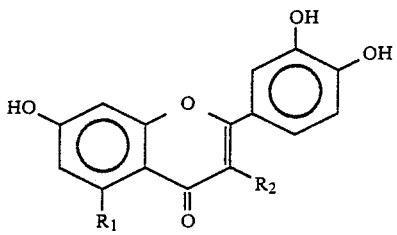

where $R_1$ is H or OH and $R_2$ is a lower alkoxy of $C_2$ to $C_6$, a cycloalkoxy of $C_5$ to $C_8$, methanesulfonyloxy or paratoluenesulfonyloxy, and $R_1$ is not OH if $R_2$ is a lower alkoxy of $C_2$ to $C_4$.

2. The compound of claim 1 wherein $R_1$ is H or OH and $R_2$ is a cycloalkoxy of $C_5$ to $C_8$, methanesulfonyloxy, or paratoluenesulfonyloxy.

3. The compound of claim 1 wherein $R_1$ is H and $R_2$ is a lower alkoxy of $C_2$ to $C_6$.

4. The compound of claim 1 wherein $R_1$ is OH and $R_2$ is methanesulfonyloxy or paratoluenesulfonyloxy.

5. The compound of claim 1 wherein $R_1$ is H and $R_2$ is methanesulfonyloxy or paratoluenesulfonyloxy.

6. A pharmaceutical composition for the lowering of blood sugar, comprising a hypoglycemic effective amount of the compound of claim 1.

7. A curative treatment for patients suffering from diabetes which comprises administering to said patient the pharmaceutical composition of claim 6.

8. A preventative treatment for patients suffering from diabetes which comprises administering to said patient the pharmaceutical composition of claim 6.

9. A pharmaceutical composition for inhibiting aldose reductase, comprising an amount of a compound of claim 1 effective for the inhibition of aldose reductance.

10. A pharmaceutical hypolipidemic composition, comprising a hypolipidemic effective amount of a compound of claim 1.

* * * * *